United States Patent [19]

Kroenke

[11] 4,410,462
[45] Oct. 18, 1983

[54] DIDODECYLDIMETHYLAMMONIUM MOLYBDATES

[75] Inventor: William J. Kroenke, Brecksville, Ohio

[73] Assignee: The B. F. Goodrich Company, Akron, Ohio

[21] Appl. No.: 402,477

[22] Filed: Jul. 28, 1982

[51] Int. Cl.$^3$ ............................................. C07F 11/00
[52] U.S. Cl. .......................... 260/429 R; 260/45.75 R
[58] Field of Search ..................................... 260/429 R

[56] References Cited

U.S. PATENT DOCUMENTS

| | | | |
|---|---|---|---|
| 3,223,625 | 12/1965 | Cyphers et al. | 260/429 R X |
| 3,290,245 | 12/1966 | Elliott et al. | 260/429 R X |
| 3,349,102 | 10/1967 | Marzluff | 260/429 R |
| 4,053,455 | 10/1977 | Kroenke | 260/429 R |
| 4,153,792 | 5/1979 | Kroenke | 260/429 R X |
| 4,217,292 | 8/1980 | Kroenke | 260/429 R |
| 4,234,474 | 11/1980 | Kroenke | 260/429 R X |
| 4,235,770 | 11/1980 | Kroenke | 260/429 R X |
| 4,247,451 | 1/1981 | Kroenke | 260/429 R X |
| 4,248,766 | 2/1981 | Kroenke | 260/429 R X |
| 4,248,767 | 2/1981 | Kroenke | 260/429 R X |

*Primary Examiner*—Helen M. S. Sneed
*Attorney, Agent, or Firm*—James R. Lindsay

[57] ABSTRACT

Didodecyldimethylammonium molybdates having the empirical formula $$[(CH_3)_2(C_{12}H_{25})_2N]_a Mo_b O_c$$

where a, b and c are (2,6,19); (6,7,24) or (4,8,26) are disclosed as novel amine molybdates which are useful as smoke retardant additives for vinyl chloride polymer compositions.

4 Claims, No Drawings

DIDODECYLDIMETHYLAMMONIUM MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 4 hours.

Amine molybdates also may be produced, as described in U.S. Pat. No. 4,217,292, by reacting essentially stoichiometric quantities of molybdenum trioxide with an amine or an amine salt in an aqueous medium essentially free of acid and in which a water-soluble ammonium or monovalent metal or divalent metal or trivalent rare earth metal salt of an inorganic or organic acid is dissolved. Sometimes the reaction is carried out in a polar organic solvent instead of water.

The particular amine molybdate formed may depend upon which process is used to form the amine molybdate and the quantity of reactants present in the reaction mixture, as well as the reaction conditions.

SUMMARY OF THE INVENTION

The present invention pertains to a class of novel molybdates, namely, didodecyldimethylammonium molybdates, which may be represented by the formula:

$$[(CH_3)_2(C_{12}H_{25})_2N]_aMo_bO_c$$

where a, b and c are (2,6,19); (6,7,24) or (4,8,26). Like many other amine molybdates, the didodecyldimethylammonium molybdates function as effective smoke retardant additives for vinyl chloride polymers.

DETAILED DESCRIPTION OF THE INVENTION

Didodecyldimethylammonium molybdates may be produced by reacting ammonium dimolybdate $[(NH_4)_2Mo_2O_7]$ and didodecyldimethylammonium bromide $[(CH_3)_2(C_{12}H_{25})]_2NBr$ in an acidic aqueous medium. Suitable acids include inorganic acids, such as hydrochloric acid, nitric acid, sulfuric acid, and the like, or mixtures thereof. The amount of acid used may be varied widely from about ½ to 10 or more molar equivalents of acid per molar equivalent of ammonium dimolybdate. However, about a 1/1 molar equivalent ratio is preferred. Sufficient water is included in the reaction mixture to insure a reaction medium that has a consistency that enables it to be easily stirred. The mixture is heated to reflux and refluxed for about 10 minutes to 16 hours, preferably while being stirred continuously. After the reaction is completed, the solid reaction product is separated from the aqueous medium by filtration, centrifugation, or other suitable separation procedure. The recovered solid reaction product desirably is washed with water and then is dried. The molar ratio of ammonium dimolybdate to didodecyldimethylammonium bromide will influence the didodecyldimethylammonium molybdate product formed as a result of the reaction. Theoretical molybdate/didodecyldimethylammonium bromide molar ratios from 0.5/1 to 3/1 are used. However, the actual molar ratios that can be used in the reaction can be outside the stated range.

The didodecyldimethylammonium molybdates within the scope of the present invention are didodecyldimethylammonium hexamolybdate $[(CH_3)_2(C_{12}H_{25})_2N]_2Mo_6O_{19}$, didodecyldimethylammonium heptamolybdate $[(CH_3)_2(C_{12}H_{25})_2N]_6Mo_7O_{24}$, and didodecyldimethylammonium octamolybdate $[(CH_3)_2(C_{12}H_{25})_2N]_4Mo_8O_{26}$.

The following examples more fully illustrate the preparation of the novel didodecyldimethylammonium molybdates of the present invention.

EXAMPLE I 2.13 grams of a 37 percent hydrochloric acid solution were mixed with 200 milliliters of water and were added to a 500 milliliter round-bottom flask equipped with a water-cooled condenser and a mechanical stirrer. 10.00 grams of didodecyldimethylammonium bromide was added to the flask and the contents of the flask were heated to reflux. 7.35 grams of ammonium dimolybdate were dissolved in 50 milliliters of hot water. The resulting cloudy hot solution was added to the flask. The mixture within the flask was heated to reflux and refluxed for 30 minutes while being stirred continuously. The contents of the flask was filtered through a Buchner funnel. The fine white powder remaining on the filter paper was washed three times with 25 milliliters of water and dried in a vacuum oven maintained at about 75° C. for 16 hours. 13.87 grams of residue was recovered. The residue was identified by infrared analysis to be didodecyldimethylammonium beta-octamolybdate.

EXAMPLE II 2.72 grams of didodecyldimethylammonium octamolybdate and 20 milliliters of acetonitrile were added to a 50 milliliter Erlenmeyer flask and stirred until the didodecyldimethylammonium octamolybdate was dispersed. 0.08 gram of concentrated sulfuric acid was mixed with 3 milliliters of water and added to the flask. The contents of the flask were warmed and stirred for two hours. The contents of the flask were cooled to room temperature (about 25° C.). A yellow precipitate formed. The contents of the flask were filtered. The yellow residue was dried in a vacuum oven at 40° C. for 16 hours. Infrared analysis identified the yellow solid as didodecyldimethylammonium hexamolybdate.

The didodecyldimethylammonium molybdates have been found to be smoke retardant additives for vinyl chloride polymer compositions. Preferably, from about 0.1 to about 20 parts by weight of a didodecyldimethylammonium molybdate is used per 100 parts by weight of vinyl chloride polymer.

Vinyl chloride polymers with which the didodecyldimethylammonium molybdates can be used as smoke retardant additives include homopolymers, copolymers and blends of homopolymers and/or copolymers, and include chlorinated polymers thereof. The vinyl chloride polymers may contain from 0 to 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene, and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate, vinyl laurate, alkyl acetate, and the like; vinyl aromatics such as styrene, α-methyl styrene, chlorostyrene, vinyl toluene, vinyl naphthalene, and the like; vinyl allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the α-β- and α-cyanopropyl acrylate, and the like; olefinically unsaturated acids and esters thereof including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecylacrylate, methoxyethyl acrylate, ethoxyethyl acrylate, hexylthioethyl acrylate, methyl methacrylate, ethyl methacrylate, butyl methacrylate, and the like.

The vinyl chloride polymer, in addition to the didodecyldimethylammonium molybdate, may contain the usual compounding ingredients known to the art such as fillers, stabilizers, opacifiers, lubricants, processing aids, impact modifiers, plasticizers, antioxidants, and the like.

Smoke retardancy may be measured using an NBS Smoke Chamber according to procedures described in ASTM E662-79 "Test For Specific Optical Density Of Smoke Generated By Solid Materials". Maximum smoke density (Dm) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100$$

The term "Dm/g" means maximum smoke density per gram of material. Dm and other aspects of the physical optics of light transmission through smoke are discussed fully in the ASTM publication.

Smoke retardance may be measured quickly using the Goodrich Smoke-Char Test. Test samples may be prepared by dry blending polymer resin and smoke retardant additives. The blend is ground in a liquid nitrogen-cooled grinder to assure uniform dispersion of the smoke retardant additives in the resin. Small (about 0.3 g) samples of the polymer blend are pressed into pellets about ¼ inch diameter for testing. Alternatively, test samples may be prepared by blending resin, smoke retardant additives and lubricant(s) or processing aid(s) in a blender such as an Osterizer blender. The blend is milled, pressed into sheets, and cut into small (about 0.3 gram) samples for testing. The test samples are placed on a screen and burned for 60 seconds with a propane gas flame rising vertically from beneath the samples. Sample geometry at a constant weight has been found not to be significant for the small samples used in this test. A Bernz-O-Matic pencil flame burner head is used with gas pressure maintained at about 40 psig. Each sample is immersed totally and continuously in the flame. Smoke from the burning sample rises in a vertical chimney and passes through the light beam of a Model 407 Precision Wideband Photometer (Grace Electronics, Inc., Cleveland, Ohio) coupled with a photometer integrator. Smoke generation is measured as integrated area per gram of sample.

The smoke retardant property of didodecyldimethylammonium molybdates is illustrated by the following examples:

EXAMPLE IV

The following recipe was used:

| Material | Parts by Wt. |
| --- | --- |
| Polyvinyl Chloride resin* | 100.0 |
| Lubricant** | 2.0 |
| Tin Stabilizer*** | 2.0 |
| Didodecyldimethylammonium molybdate | 5.0 |

*Homopolymer of vinyl chloride having an inherent viscosity of about 0.98–1.04; ASTM classification GO-5-15543.
**A commercial polyethylene powder lubricant (Microthene 510).
***Tin Thioglycolate 5.0 grams of the didodecyldimethylammonium beta-octamolybdate of Example I were mixed with 100.0 grams of the polyvinyl chloride resin of the aforesaid recipe on a two-roll mill. The lubricant and tin stabilizer of the recipe were added to the molybdate/polyvinyl chloride resin mixture and the resulting composition was milled on the mill for about 5 minutes at a roll temperature of about 165° C. The milled composition was pressed into a 6×6×0.05 inch sheet. Pressing was done at about 160° C. for 5 minutes using 40,000 pounds (about 14,900 kg) of force applied to a 4-inch ram. The sample (Sample 1) received a 2-minute preheat before being pressed.

The molded sample was cut into 2−7/8×2−7/8×0.50 inch sections and tested against a control sample formed utilizing the aforesaid recipe but without use of the molybdate additive. Testing was performed using the flaming mode of the NBS Smoke Chamber Test (ASTM E662-79) described hereinabove. The test results are given in Table I.

TABLE I

| Sample | Dm/g* | Smoke Reduction (%) |
| --- | --- | --- |
| Control | 60.8 | — |
| 1 | 28.0 | 53.9 |

*Dm/g = maximum smoke density per gram of sample.

0.075 gram of the didodecyldimethylammonium hexamolybdate of Example II was blended in a liquid nitrogen-cooled grinder with 1.50 grams of polyvinyl chloride resin (homopolymer of vinyl chloride having an inherent viscosity of about 0.98–1.04, ASTM classification GO-5-15543) as described above. The mixture (Sample 2) was cold pressed into ¼ inch diameter pellets weighing about 0.3 gram each.

Testing for smoke reduction was performed using the Goodrich Smoke-Char Test described above. The test results are set forth in Table II.

TABLE II

| Sample | Spvc* | Smoke Reduction (%) |
| --- | --- | --- |
| Control | 74.8 | — |
| 2 | 43.2 | 42.2 |

*Smoke-char smoke number per gram of polyvinyl chloride resin in sample blend.

The improved smoke retardant vinyl chloride polymer compositions obtained by the inclusion of a didodecyldimethylammonium molybdate in the composition are useful wherever smoke reduction is a desirable property, such as in carpeting, house siding, plastic components for aircraft and passenger car interiors, and the like.

I claim:

1. Didodecyldimethylammonium molybdates having the empirical formula $$[(CH_3)_2(C_{12}H_{25})_2N]_a Mo_b O_c$$

where a, b and c are (2,6,19); (6,7,24) or (4,8,26).

2. The didodecyldimethylammonium molybdate of claim 1 wherein a is 2, b is 6 and c is 19.

3. The didodecyldimethylammonium molybdate of claim 1 wherein a is 6, b is 7 and c is 24.

4. The didodecyldimethylammonium molybdate of claim 1 wherein a is 4, b is 8 and c is 26.

* * * * *